US00PP34406P2

(12) United States Plant Patent
Pineau

(10) Patent No.: US PP34,406 P2
(45) Date of Patent: Jul. 5, 2022

(54) ***PRUNUS* PLANT NAMED 'MINIREDIA'**

(50) Latin Name: *Prunus laurocerasus*
Varietal Denomination: 'Miniredia'

(71) Applicant: Hortival Diffusion SAS, Beaufort en Valee (FR)

(72) Inventor: Patrick Pineau, Saint Mathurin sur Loire (FR)

(73) Assignee: Hortival Diffusion SAS

( * ) Notice: Subject to any disclaimer, the term of this patent is extended or adjusted under 35 U.S.C. 154(b) by 0 days.

(21) Appl. No.: 17/355,900

(22) Filed: Jun. 23, 2021

(51) Int. Cl.
*A01H 5/00* (2018.01)
*A01H 6/74* (2018.01)

(52) U.S. Cl.
USPC ..... Plt./226

(58) Field of Classification Search
USPC ..... Plt./156, 182, 226
See application file for complete search history.

*Primary Examiner* — Susan McCormick Ewoldt

(57) ABSTRACT

A new and distinct *Prunus* cultivar named 'MINIREDIA' is disclosed, characterized by a rounded and very compact plant habit. Young foliage is distinctively tinged a strong greyed-orange color. Mature foliage is rounded and dark green. Plants are tolerant to *Pseudomonas syringae*. The new cultivar is a *Prunus*, suitable for ornamental garden purposes.

4 Drawing Sheets

Latin name of the genus and species: *Prunus laurocerasus*.

Variety denomination: 'MINIREDIA'.

BACKGROUND OF THE INVENTION

The new cultivar is a product of breeding program with the intent to produce dwarf *Prunus* varieties with interesting colors. The new variety is the result of a crossing made in La Menitre, France in May of 2007. The seed parent is an undistributed, unpatented proprietary seedling referred to as 'N4281', the pollen parent is the unpatented *Prunus laurocerasus* 'Caucasica nana'. The new variety was selected in July of 2012 at a commercial nursery in La Menitre, France.

'Miniredia' was first propagated by softwood cuttings at the commercial nursery in La Menitre, France in October of 2012. Subsequent generations have been reproduced and have shown that the unique features of this cultivar are stable and reproduced true to type.

SUMMARY OF THE INVENTION

The cultivar 'MINIREDIA' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MINIREDIA' These characteristics in combination distinguish 'MINIREDIA' as a new and distinct *Prunus* cultivar:

1. Rounded and very compact plant habit.
2. Young foliage has a strong Greyed-Orange Color.
3. Thick, rounded mature foliage of dark green.
4. Tolerant to *Pseudomonas syringae*.

COMPARISON TO PARENT VARIETIES

Plants of the new cultivar 'MINIREDIA' are similar to plants of the parent varieties; *Prunus laurocerasus* 'N4281' and 'Caucasica nana' in most horticultural characteristics, however, differences are noted in the following tables:

TABLE 1

| NEW CULTIVAR *Prunus laurocerasus* 'Miniredia' | FEMALE PARENT *Prunus laurocerasus* 'N4281' |
|---|---|
| 1. Dwarf growth habit | Medium growth habit |
| 2. Large oblong leaves | Elliptic leaves |
| 3. Dark green leaf color | Medium green leaf color |
| 4. Entire to slightly serrate margin | Serrate margin |

TABLE 2

| NEW CULTI VAR *Prunus laurocerasus* 'Miniredia' | MALE PARENT *Prunus laurocerasus* 'Caucasica nana' |
|---|---|
| 1. Dwarf growth habit | Moderate growth habit |
| 2. Dark green leaf color | Medium green leaf color |
| 3. Orange-red young leaf | Green young leaf |
| 4. Rounded fruit form | Olive fruit form |
| 5. Large oblong leaf | Elliptic leaf, more elongate |

COMMERCIAL COMPARISON

'MINIREDIA' can be compared to the commercial variety *Prunus laurocerasus* 'Mount Vernon', unpatented. Plants of the new cultivar 'MINIREDIA' are similar to plants of 'Mount Vernon' in most horticultural characteristics, however, plants of the new cultivar 'MINIREDIA' differ in the following:

1. The new variety has oblong foliage; this comparator has elliptic foliage.
2. The new variety has a mounding habit, as a shrub, this comparator has a spreading habit, like a groundcover.
3. New shoots of 'Miniredia' produce orange-red foliage, this comparator has light green new growth.

'MINIREDIA' can be compared to the commercial variety *Prunus laurocerasus* 'Otto Luyken' unpatented. Plants of the new cultivar 'MINIREDIA' are similar to plants of 'Otto Luyken' in most horticultural characteristics, however, plants of the new cultivar 'MINIREDIA' differ in the following:

1. The new variety has oblong foliage; this comparator has elliptic foliage.
2. The new variety has a smaller habit, than this comparator.

BRIEF DESCRIPTION OF THE PHOTOGRAPHS

The accompanying photograph in FIG. 1 illustrates in full color a typical plant of 'MINIREDIA' grown outdoors in Grand Haven, Mich.

Figure 1:
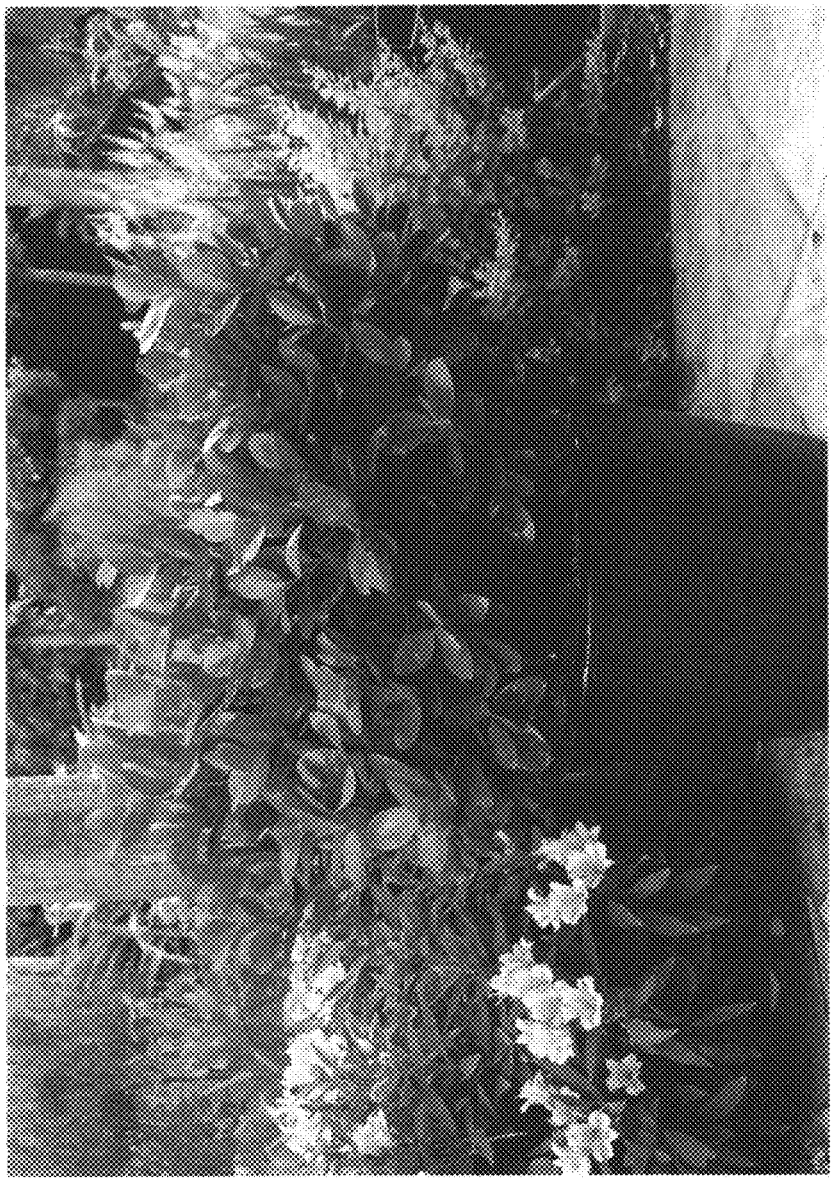
Figure 2:
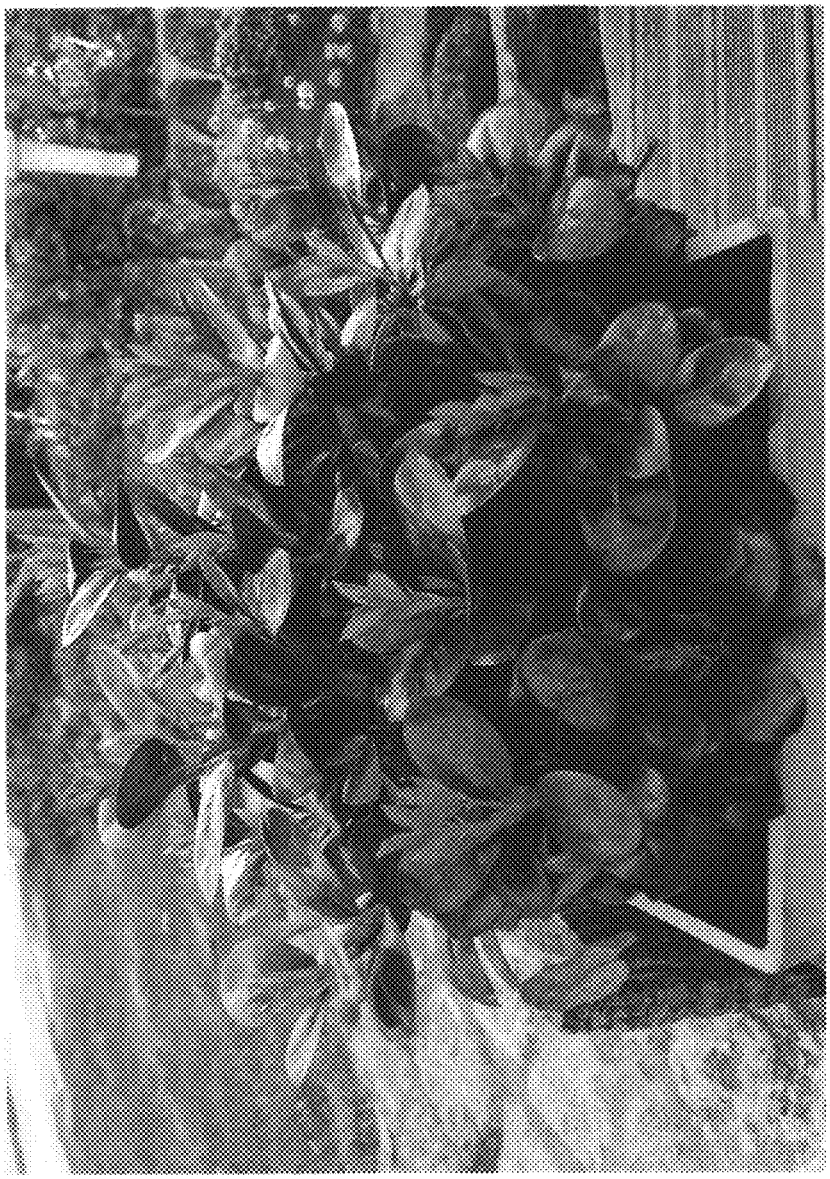
FIG. 2 illustrates in full color a close up of the foliage. The plants in FIGS. 1 and 2 are approximately 2 years old.
Figure 3:
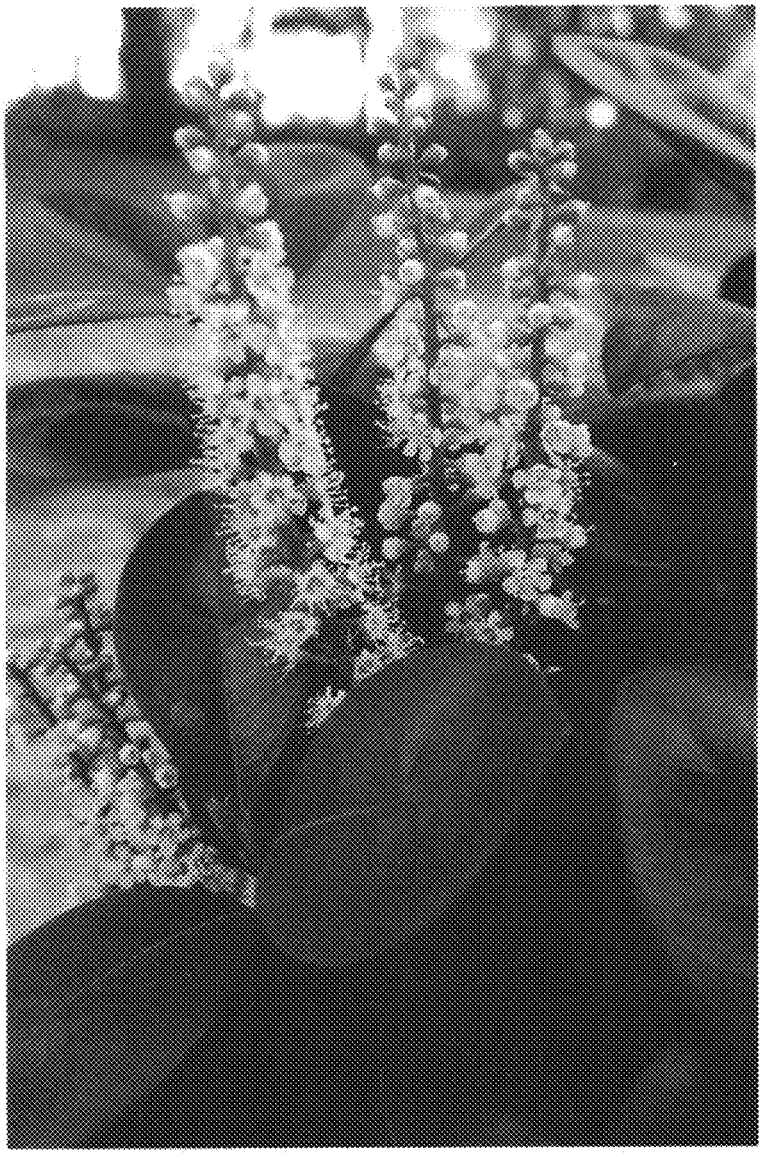
FIG. 3 illustrates inflorescences of the new variety.
Figure 4:
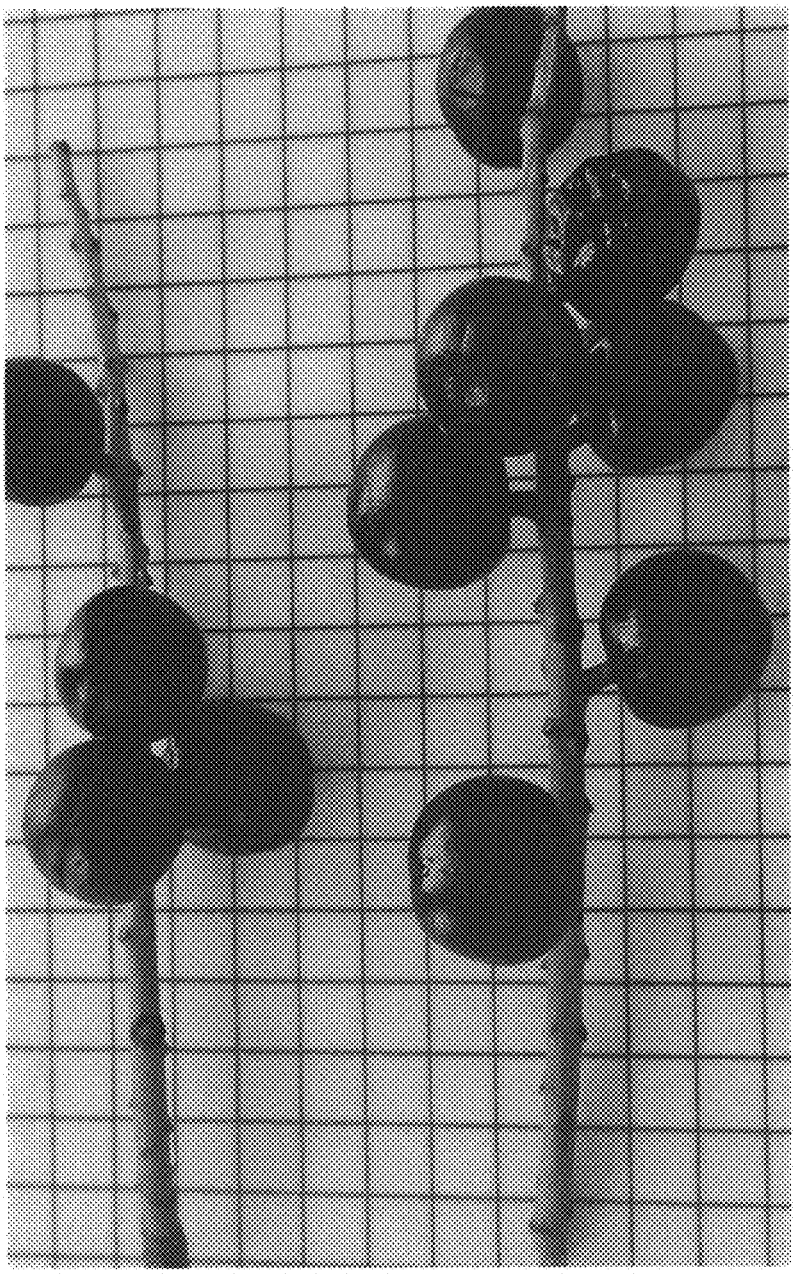
FIG. 4 illustrates fruits of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'MINIREDIA' plants grown in a polyhouse in Grand Haven, Mich. Plants are approximately 4 to 7 years old, in a 5 gallon nursery container. Temperatures ranged from about 5° C. to 10° C. at night and 18° C. to 27° C. during the day. Measurements and numerical values represent averages of typical plant types.

Botanical classification: *Prunus laurocerasus* 'MINIREDIA'.

PROPAGATION

Time to produce a rooted young plant: Approximately 3 months at 18° C. to 27° C. from semi-hardwood cuttings.

Root description: Fine, fibrous young roots. Older roots becoming woody. Tan and brown in color, not accurately measured with R.H.S. chart.

PLANT

Growth habit: Upright and slightly spreading evergreen shrub. Compact and dwarf.

Shape: Globular.

Height: Approximately 60 cm.

Plant spread: Approximately 40 cm.

Branching characteristics: Free branching, both basal and lateral branches.

Length of lateral branches: Approximately 50 cm.

Diameter of lateral branches: Approximately 3 mm.

Lateral branch angle: 45 to 90 degrees from center.

Lateral branch color: Young branches near RHS Yellow-Green 144B. Mature branches: Near RHS Brown N200A.

Stem texture: No pubescence observed.

Number of leaves per lateral branch: Average 25 to 45.

Internode length: Average 1.75 cm.

Age of plant described: Approximately 2 to 3 years.

FOLIAGE

Leaf:

*Type*.—Simple.

*Arrangement*.—Sub-opposite to alternate.

*Average length*.—Approximately 7.75 cm.

*Average width*.—Approximately 4.5 cm.

*Shape of blade*.—Elliptic.

*Apex*.—Acute to cuspidate.

*Base*.—Rounded.

*Attachment*.—Short petiolate.

*Margin*.—Entire, slightly serrate towards apex.

*Aspect*.—Weak upward fold from center vein.

*Texture of top surface*.—Smooth.

*Texture of bottom surface*.—Smooth.

*Appearance of top surface*.—Very glossy.

*Texture of bottom surface*.—Matte.

*Color*.—Young foliage upper side: Near RHS Yellow-Green 146B strongly tinged with Greyed-Orange 172B. Young foliage under side: Near RHS Yellow-Green 146B strongly tinged with Greyed-Orange 172B. Mature foliage upper side: Near RHS Green NN137A. Mature foliage under side: Near RHS Yellow-Green 146B.

*Venation*.—Type: Pinnate. Venation color upper side: Near Yellow-Green 146B. Venation color under side: Near RHS Yellow-Green 146B.

Petiole:

*Length*.—6 mm.

*Width*.—4 mm.

*Texture*.—Glabrous all surfaces.

*Color*.—Upper Surface: Yellow-Green 144B. Lower Surface: Yellow Green 144B.

FLOWER

Inflorescence:

*Description*.—Single flowers arranged in racemes.

*Flowering season*.—Spring.

*Flower longevity*.—2-3 weeks.

*Fragrance*.—Moderate.

*Inflorescence per branch*.—Average range 1 to 3.

*Number of flowers per inflorescence*.—About 100 to 150 per cyme.

*Inflorescence height*.—Avg. 8.0 cm.

*Inflorescence diameter*.—Avg. 2.0 cm.

*Flowers*.—Flower diameter: 8 mm. Flower depth: 5 mm. Flower Angle: Outwardly facing. Persistent of Self-Cleaning: Self-Cleaning.

*Flower bud*.—Length: 3 mm. Diameter: 2 mm. Shape: Round. Color: Near RHS White 155A.

*Petals*.—Number: 5. Arrangement: Whorl. Length: Avg. 4 mm. Width: Avg. 3.5 mm. Shape: Obovate. Apex: Obtuse. Base: Fused. Margin: Entire. Texture: Glabrous, silky upper and lower surfaces. Color: Immature upper surface: White NN155D. Immature lower surface: White NN155D. Mature upper surface: White NN155D. Mature lower surface: White NN155D.

*Calyx* (*individual sepals indistinguishable*).—Shape: Cup-shaped. Length: 3 mm. Width: 4 mm. Texture: Glabrous upper and lower surfaces. Color: Yellow-Green 1444D, upper and lower surfaces.

*Peduncle*.—Length: Avg. 4.5 cm. Width: Avg. 1.5 mm. Color: Upper section Yellow-Green 144B. Texture: Pubescent. Angle: Upright and slightly outward. Strength: Strong.

*Pedicels*.—Length: Avg. 1 mm. Diameter: Avg. 1 mm. Texture: Pubescent. Color: Yellow-Green 144B. Strength: Strong.

REPRODUCTIVE ORGANS

Gynoecium:

*Pistil number*.—1.

*Pistil length*.—Less than 1 mm.

*Stigma shape*.—Disc.

*Stigma color*.—Near RHS Yellow-White 158D.

*Style length*.—Less than 1 mm.

*Style color*.—Near RHS White 155D.

Androecium:

*Stamen number*.—5.

*Filament length*.—1 mm.

*Filament color*.—Yellow-White 158D.

*Anther shape*.—Oblong.

*Anther length*.—0.5 mm.

*Anther color*.—Yellow 6B.

*Amount of pollen*.—Scant.

*Pollen color*.—Yellow 6B.

OTHER CHARACTERISTICS

Fruit: Approximately 5 to 10 per branch. Spherical drupe 1 cm long long, 1 cm in diameter, colored Black 202A, smooth texture, glossy.

Disease and pest resistance: Tolerant to *Pseudomonas syringae* Not observed to be susceptible nor resistant to other normal diseases and pests of *Prunus laurocerasus*.

Drought tolerance: No tolerance for drought observed.

Temperature tolerance: USDA Zones 6 to 9.

What is claimed is:

1. A new and distinct cultivar of *Prunus laurocerasus* plant named 'MINIREDIA' as herein illustrated and described.

* * * * *